(12) United States Patent
Andonovski et al.

(10) Patent No.: US 11,466,874 B2
(45) Date of Patent: Oct. 11, 2022

(54) AIR FRESHENER ASSEMBLY

(71) Applicants: Steven Andonovski, Windsor (CA); Calin Dron, Windsor (CA)

(72) Inventors: Steven Andonovski, Windsor (CA); Calin Dron, Windsor (CA)

( * ) Notice: Subject to any disclaimer, the term of this patent is extended or adjusted under 35 U.S.C. 154(b) by 147 days.

(21) Appl. No.: 16/922,731

(22) Filed: Jul. 7, 2020

(65) Prior Publication Data
US 2022/0010986 A1   Jan. 13, 2022

(51) Int. Cl.
*F24F 3/16*   (2021.01)
*A61L 9/14*   (2006.01)
*A61L 9/12*   (2006.01)

(52) U.S. Cl.
CPC .................. *F24F 3/16* (2013.01); *A61L 9/12* (2013.01); *A61L 9/14* (2013.01)

(58) Field of Classification Search
None
See application file for complete search history.

(56) References Cited

U.S. PATENT DOCUMENTS

| | | | | |
|---|---|---|---|---|
| 4,159,672 A | * | 7/1979 | Garguilo | F24F 3/12 |
| | | | | 454/337 |
| 4,229,415 A | * | 10/1980 | Bryson | A01M 13/00 |
| | | | | 422/109 |
| 5,030,253 A | | 7/1991 | Tokuhiro | |
| 6,435,419 B1 | | 8/2002 | Davis | |
| 7,223,166 B1 | | 5/2007 | Wiseman, Sr. | |
| D672,859 S | | 12/2012 | Walker | |
| 8,491,843 B2 | | 7/2013 | Spano, Jr. | |
| 2010/0243754 A1 | * | 9/2010 | Harris | A01M 1/2033 |
| | | | | 239/34 |
| 2014/0097266 A1 | * | 4/2014 | Habbel | B65D 83/303 |
| | | | | 239/66 |
| 2014/0141709 A1 | * | 5/2014 | Hammer | A61L 9/12 |
| | | | | 454/284 |
| 2017/0360981 A1 | * | 12/2017 | Avidor | A61L 9/012 |

FOREIGN PATENT DOCUMENTS

WO   WO2010059047   5/2010

OTHER PUBLICATIONS

Coupled-Synonym—Merriam-Webster Thesaurus-evidentiary reference, [online] [retrieved on Jan. 26, 2022], https://www.merriam-webster.com/thesaurus/coupled (Year: 2022).*

* cited by examiner

Primary Examiner — Jelitza M Perez (57) ABSTRACT

An air freshener assembly includes a housing that is positionable on a distribution duct of a heating, ventilation and air conditioning (HVAC) system. A magnet is coupled to the housing and the magnet magnetically engages the distribution duct for retaining the housing on the distribution duct. A reservoir is positioned within the housing and the reservoir contains a chemical fragrance. A pump unit is coupled to the housing and the pump unit is in fluid communication with the reservoir to pump the chemical fragrance. The pump unit pumps a measured unit of the chemical fragrance each time the pump unit is turned on. The pump unit is in fluid communication with an interior of the distribution duct of the HVAC system to release the chemical fragrance into the distribution duct.

9 Claims, 6 Drawing Sheets

AIR FRESHENER ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to freshener devices and more particularly pertains to a new freshener device for freshening air blown by an HVAC system.

(2) Description of Related Art Including Information Disclosed Under 37 CFR 1.97 and 1.98

The prior art relates to freshener devices including a fragrance air supply that is in fluid communication with an HVAC system. The prior art also discloses an air freshener that includes a pipe which extends into a distribution duct of an HVAC system and a heater for heating fragrance released into the distribution duct. The prior art further discloses an air freshener device that includes an electronic timer for releasing a fragrance into a distribution duct of an HVAC system at pre-determined intervals of time. Additionally, the prior art discloses an air freshener system that has an intake tube that is in fluid communication with a bulk reservoir of fragrance and a supply tube that is in fluid communication with a distribution duct of an HVAC system.

BRIEF SUMMARY OF THE INVENTION

An embodiment of the disclosure meets the needs presented above by generally comprising a housing that is positionable on a distribution duct of a heating, ventilation and air conditioning (HVAC) system. A magnet is coupled to the housing and the magnet magnetically engages the distribution duct for retaining the housing on the distribution duct. A reservoir is positioned within the housing and the reservoir contains a chemical fragrance. A pump unit is coupled to the housing and the pump unit is in fluid communication with the reservoir to pump the chemical fragrance. The pump unit pumps a measured unit of the chemical fragrance each time the pump unit is turned on. The pump unit is in fluid communication with an interior of the distribution duct of the HVAC system to release the chemical fragrance into the distribution duct.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
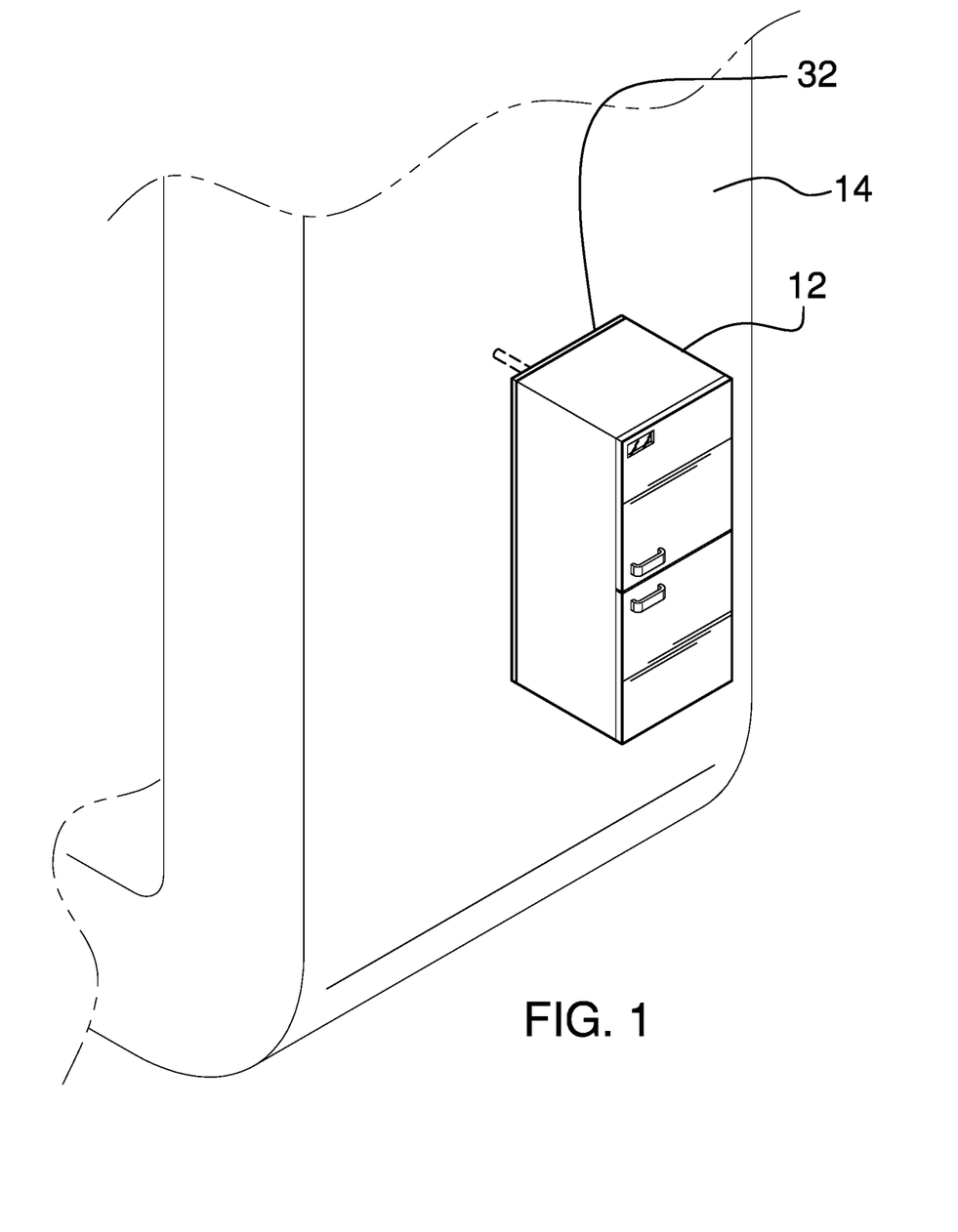
FIG. 1 is a perspective in-use view of an air freshener assembly according to an embodiment of the disclosure.
Figure 2:
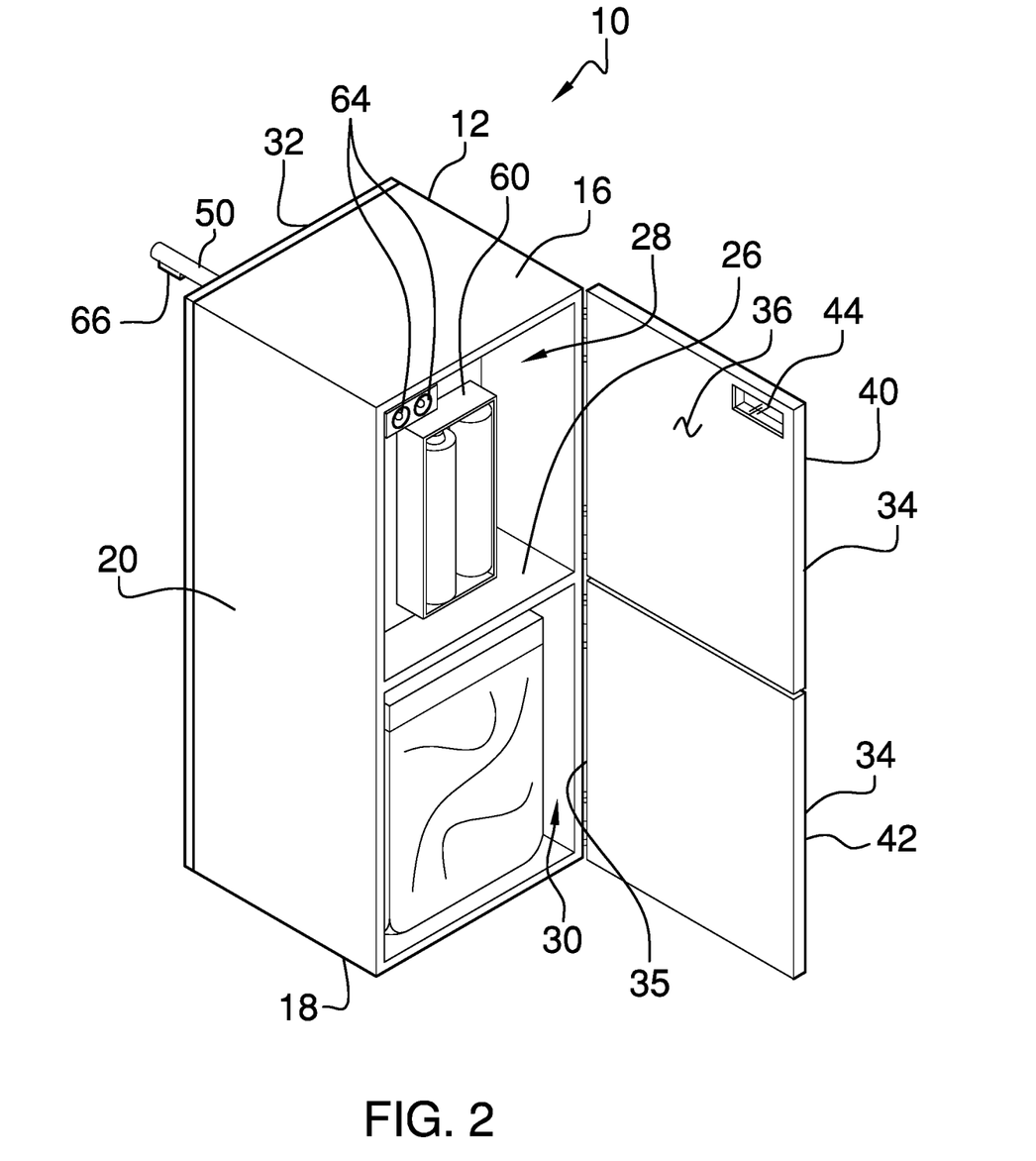
FIG. 2 is a front perspective view of an embodiment of the disclosure.
Figure 3:
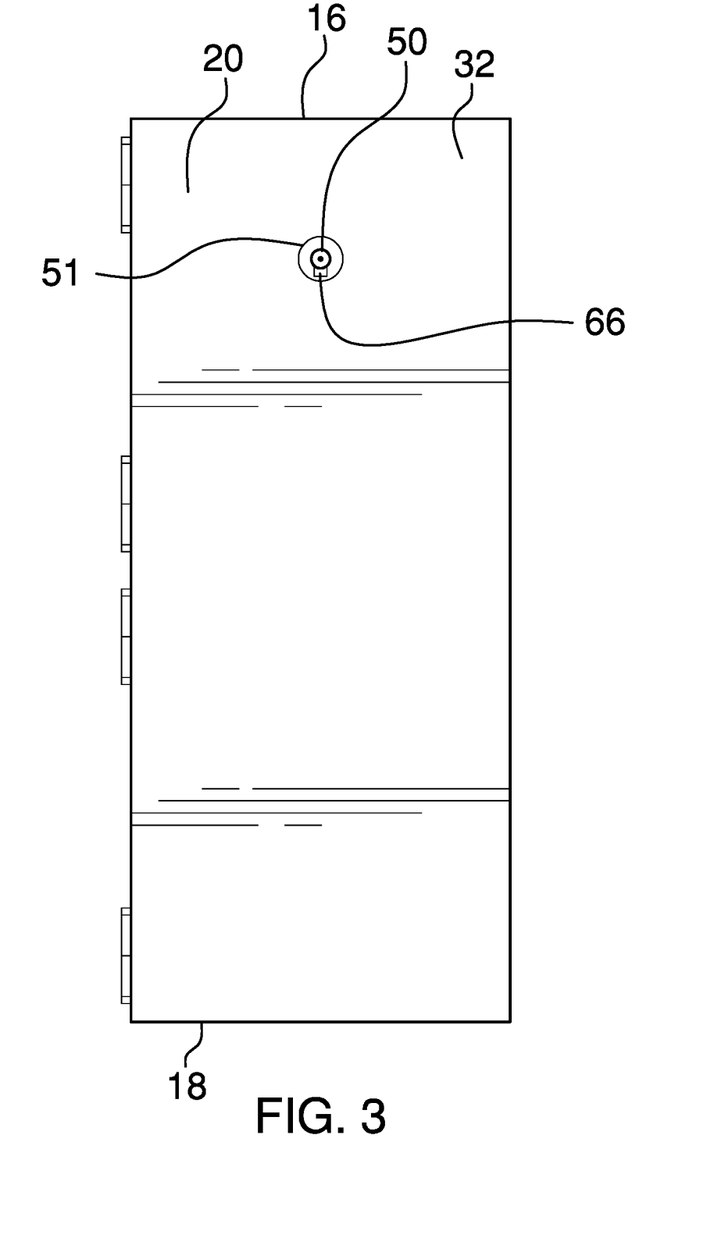
FIG. 3 is a back view of an embodiment of the disclosure.
Figure 4:
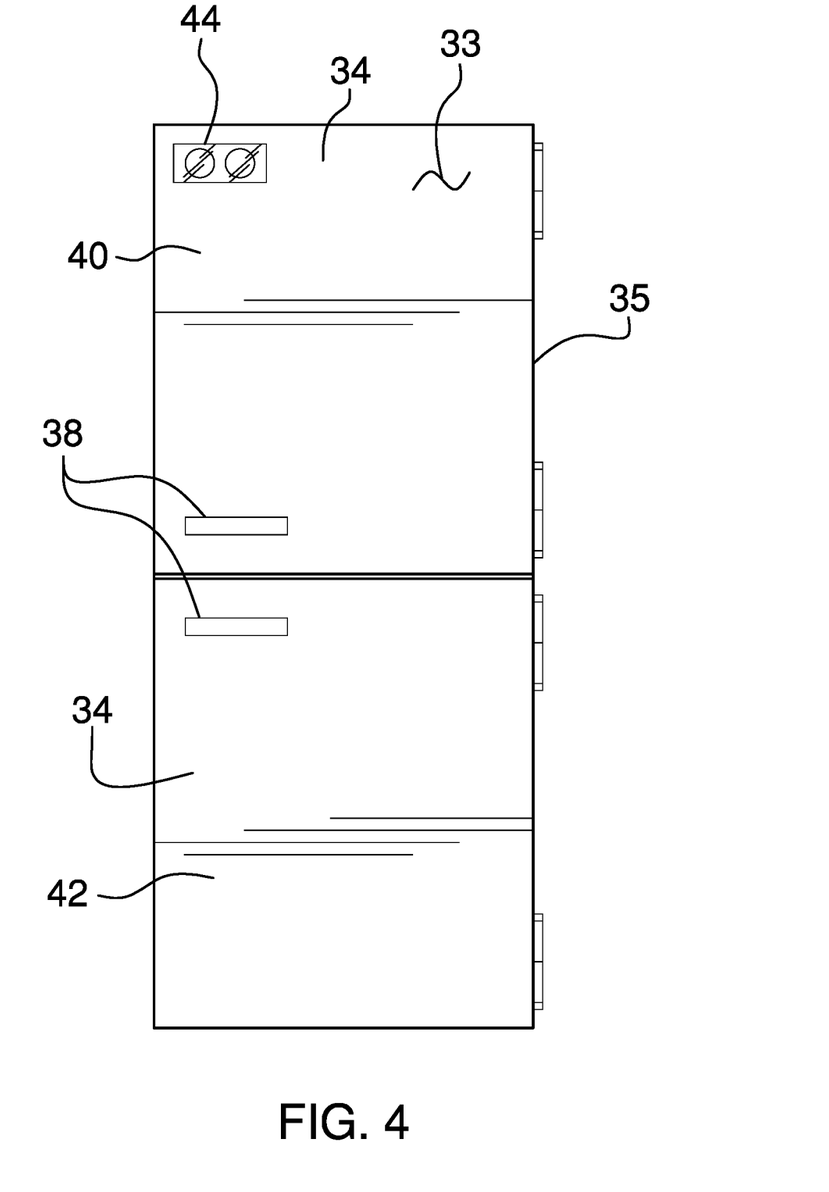
FIG. 4 is a front view of an embodiment of the disclosure.
Figure 5:
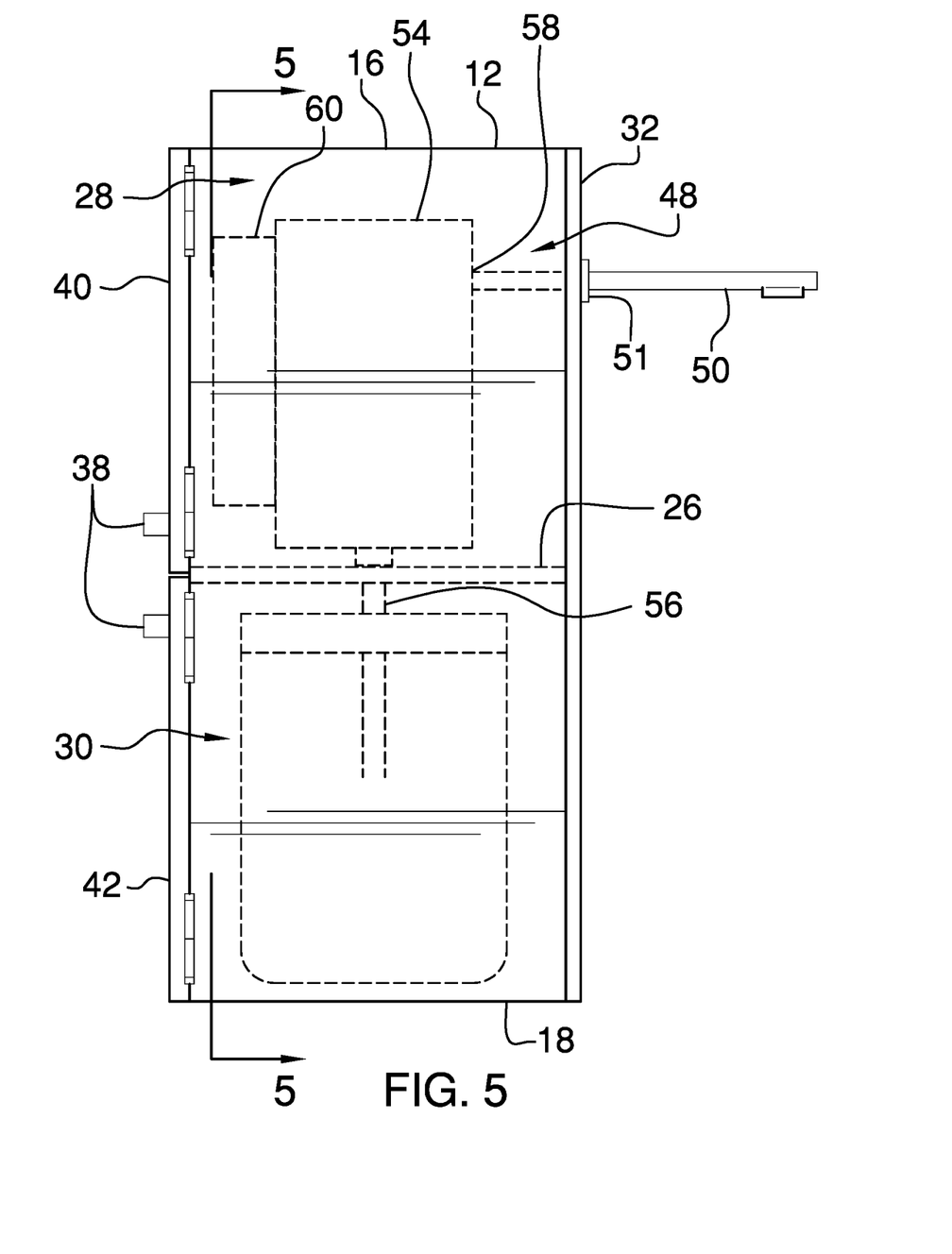
FIG. 5 is a left side phantom view of an embodiment of the disclosure.
Figure 6:
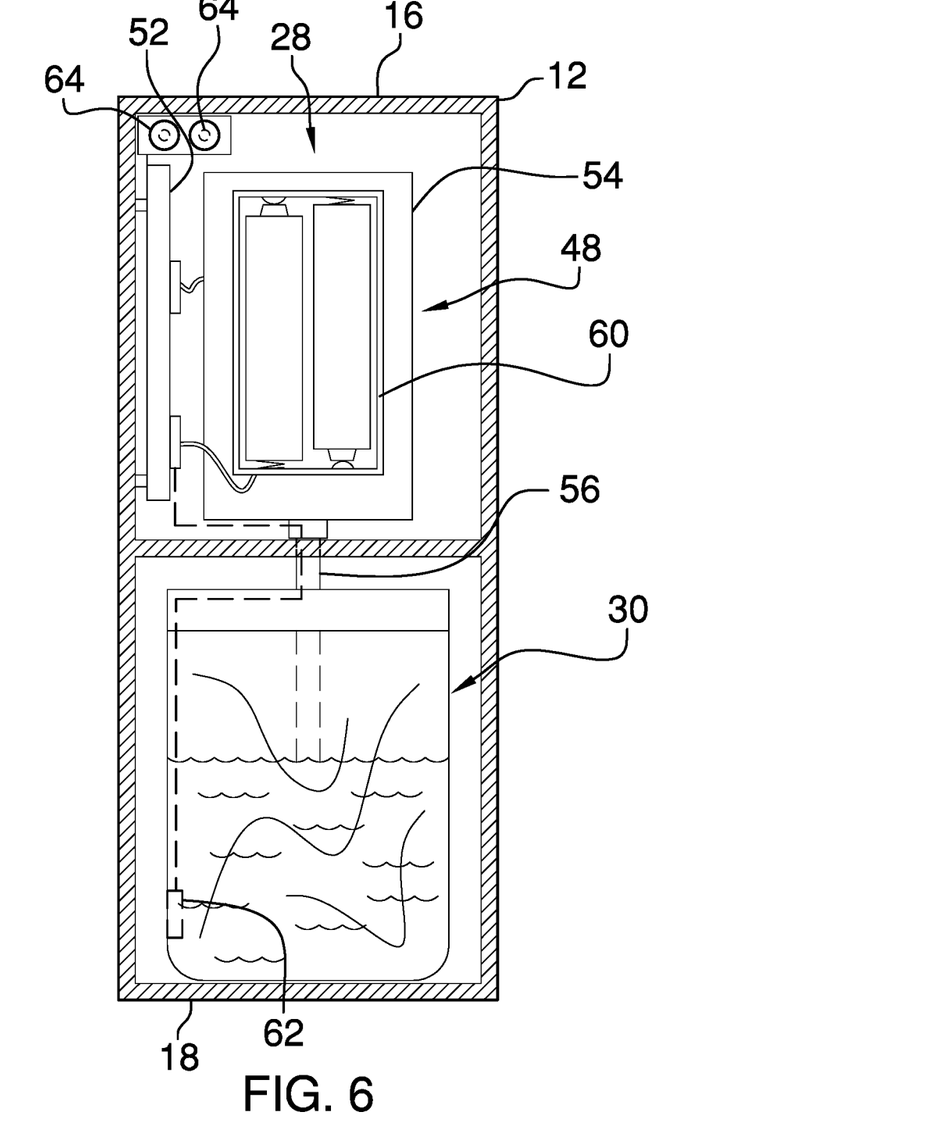
FIG. 6 is a cross sectional view taken along line 6-6 of FIG. 5 of an embodiment of the disclosure.

With reference now to the drawings, and in particular to FIGS. 1 through 6 thereof, a new freshener device embodying the principles and concepts of an embodiment of the disclosure and generally designated by the reference numeral 10 will be described.

As best illustrated in FIGS. 1 through 6, the air freshener assembly 10 generally comprises a housing 12 that is positionable on a distribution duct 14 of a heating, ventilation and air conditioning (HVAC) system. The HVAC system may be an HVAC system in a house or other similar type of building. The housing 12 has a top wall 16, a bottom wall 18 and an outer wall 20 extending therebetween. The outer wall 20 has a back side 22 and a front side 24, and the front side 24 is open into an interior of the housing 12. The housing 12 has a divider 26 therein to define a first portion 28 and a second portion 30 of an interior of the housing 12. Moreover, the divider 26 is centrally positioned between the top wall 16 and the bottom wall 18. A magnet 32 is coupled to the housing 12 and the magnet 32 magnetically engages the distribution duct 14 for retaining the housing 12 on the distribution duct 14. The magnet 32 is positioned on the back side 22 of the outer wall 20 of the housing 12.

A pair of doors 34 is each hingedly coupled to the housing 12 for opening 44 and closing the housing 12. Each of the doors 34 has a first surface 36, a second surface 33 and a first lateral edge 35, and the first lateral edge 35 of each of the doors 34 is hingedly coupled to the front side 24 of the outer wall 20 of the housing 12. The first surface 36 each of the doors 34 abuts the front side 24 when the doors 34 are closed. A pair of handles 38 is each coupled to the second surface 33 of a respective one of the doors 34 for opening 44 and closing the doors 34. The pair of doors 34 includes an upper door 40 and a lower door 42, and the upper door 40 has an opening 44 extending therethrough. The upper door 40 is aligned with the first portion 28 of the interior of the housing 12 and the lower door 42 is aligned with the second portion 30 of the interior of the housing 12.

A reservoir 46 is positioned within the housing 12 and the reservoir 46 contains a chemical fragrance. The chemical fragrance may comprise an aerosol air freshener or other type of chemical fragrance that is approved for household use. Additionally, the chemical fragrance may have a floral scent or other pleasing scent commonly associated with air fresheners. Additionally, the reservoir 46 is positioned in the second portion 30 of the interior of the housing 12. The reservoir 46 may be an aerosol canister that is manufactured specifically for use in the assembly disclosed in this application, or the reservoir 46 may be an aerosol fragrance reservoir of any conventional design.

A pump unit 48 is coupled to the housing 12 and the pump unit 48 is in fluid communication with the reservoir 46 to pump 54 the chemical fragrance. The pump unit 48 pumps a measured amount of the chemical fragrance each time the pump unit 48 is turned on. Additionally, the pump unit 48 is in fluid communication with an interior of the distribution duct 14 of the HVAC system to release the chemical fragrance into the distribution duct 14. The pump unit 48 comprises a pipe 50 extending through the back side 22 of the outer wall 20 of the housing 12. The pipe 50 extends into the distribution duct 14 of the HVAC system and the pipe 50 is aligned with the first portion 28 of the interior of the housing 12. A gasket 51 is positioned around the pipe 50 and the gasket 51 forms a seal with the distribution duct 14 when the pipe 50 is extended therethrough.

The pump unit 48 includes a control circuit 52 that is positioned in the housing 12 and the control circuit 52 receives a pump input. The pump unit 48 includes a pump 54 that has an inlet 56 and an outlet 58. The inlet 56 is fluidly coupled to the reservoir 46 and the outlet 58 is fluidly coupled to the pipe 50 to release the chemical fragrance into the distribution duct 14. The pump 54 is electrically coupled to the control circuit 52 and the pump 54 is turned on when the control circuit 52 receives the pump input. The pump 54 pumps a fixed quantity of the chemical fragrance each time the pump 54 is turned on and the pump 54 is positioned in the first portion 28 of the interior of the housing 12. Additionally, the pump 54 may be an electric fluid pump of any conventional design.

The pump unit 48 includes a power supply 60 that is positioned in the housing 12. The power supply 60 is electrically coupled to the control circuit 52 and the power supply 60 comprises at least one battery. The power supply 60 is positioned in the first portion 28 of the interior of the housing 12. A level sensor 62 is positioned within the reservoir 46 wherein the level sensor 62 is configured to sense the level of chemical fragrance in the reservoir 46. Additionally, the level sensor 62 is electrically coupled to the control circuit 52.

A pair of light emitters 64 is included and each of the light emitters 64 is positioned in the housing 12. Each of the light emitters 64 is electrically coupled to the control circuit 52 and each of the light emitters 64 emits a unique color of light. Each of the light emitters 64 is assigned to a respective one of the level sensor 62 and the power supply 60. The light emitter 64 assigned to the level sensor 62 is turned on when the level sensor 62 senses a minimum level of chemical fragrance in the reservoir 46. The light emitter 64 assigned to the power supply 60 is turned on when the power supply 60 falls below a minimum charge level. Additionally, each of the light emitters 64 is aligned with the opening 44 in the door positioned on the first portion 28 of the interior of the housing 12 such that each of the light emitters 64 is visible to a user.

An air sensor 66 is coupled to the pipe 50 such that the air sensor 66 is positioned within the distribution duct 14 of the HVAC system. In this way the air sensor 66 is in fluid communication with an interior of the distribution duct 14. The air sensor 66 is electrically coupled to the control circuit 52 and the control circuit 52 receives the pump input when the air sensor 66 senses air is moved in the distribution duct 14. The air sensor 66 may comprise an electronic air sensor or the like that can sense movement of air within the distribution duct 14.

In use, the pump 54 is turned on each time air sensor 66 senses that air is being blown in the distribution duct 14 when the HVAC system is turned on. In this way the measured amount of the chemical fragrance is released into the distribution duct 14. Thus, the air blown by the HVAC system is imbued with a pleasing fragrance. The reservoir 46 in the housing 12 is replaced when the chemical fragrance is depleted.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. An air freshener assembly being integrated into an air conditioning system of a building for freshening air blown by the air conditioning system, said assembly comprising:
   a housing being positionable on a distribution duct of a heating, ventilation and air conditioning (HVAC) system, said housing has a top wall, a bottom wall and an outer wall extending therebetween, said outer wall having a back side and a front side, said front side being open into an interior of said housing, said housing having a divider therein to define a first portion and a second portion of an interior of said housing, said divider being centrally positioned between said top wall and said bottom wall;
   a magnet being coupled to said housing, said magnet magnetically engaging the distribution duct for retaining said housing on the distribution duct, said magnet being positioned on said back side of said outer wall of said housing;

a pair of doors, each of said doors being hingedly coupled to said housing for opening and closing said housing;

a pair of handles, each of said handles being coupled to a second surface of a respective one of said doors for opening and closing said doors;

a reservoir being positioned within said housing, said reservoir containing a chemical fragrance; and a pump unit being coupled to said housing, said pump unit being in fluid communication with said reservoir wherein said pump unit is configured to pump the chemical fragrance, said pump unit pumping a measured unit of the chemical fragrance each time said pump unit is turned on, said pump unit being in fluid communication with an interior of the distribution duct of the HVAC system wherein said pump unit is configured to release the chemical fragrance into the distribution duct, wherein said pump unit comprises a pipe extending through said back side of said outer wall of said housing and through said magnet, said pipe extending into the distribution duct of the HVAC system, said pipe being aligned with said first portion of said interior of said housing.

2. The assembly according to claim 1, wherein each of said doors has a first surface, said second surface and a first lateral edge, said first lateral edge of each of said doors being hingedly coupled to said front side of said outer wall of said housing, said first surface each of said doors abutting said front side when said doors are closed.

3. The assembly according to claim 2, wherein said pair of doors includes an upper door and a lower door, said upper door having an opening extending therethrough, said upper door being aligned with said first portion of said interior of said housing, said lower door being aligned with said second portion of said interior of said housing.

4. The assembly according to claim 1, wherein said pump unit includes:

a control circuit being positioned in said housing, said control circuit receiving a pump input; and a pump having an inlet and an outlet, said input being fluidly coupled to said reservoir, said outlet being fluidly coupled to said pipe wherein said pipe is configured to release the chemical fragrance into the distribution duct, said pump being electrically coupled to said control circuit, said pump being turned on when said control circuit receives said pump input, said pump pumping a fixed quantity of the chemical fragrance each time said pump is turned on, said pump being positioned in said first portion of said interior of said housing.

5. The assembly according to claim 4, wherein said pump unit includes a power supply being positioned in said housing, said power supply being electrically coupled to said control circuit, said power supply comprising at least one battery, said power supply being positioned in said first portion of said interior of said housing.

6. The assembly according to claim 4, wherein said pump unit includes a level sensor being positioned within said reservoir wherein said level sensor is configured to sense the level of chemical fragrance in said reservoir, said level sensor being electrically coupled to said control circuit.

7. The assembly according to claim 6, wherein said pump unit includes:

a power supply being positioned in said housing; and a pair of light emitters, each of said light emitters being positioned in said housing, each of said light emitters being electrically coupled to said control circuit, each of said light emitters emitting a unique color of light, each of said light emitters being assigned to a respective one of said level sensor and said power supply, said light emitter assigned to said level sensor being turned on when said level sensor senses a minimum level of chemical fragrance in said reservoir, said light emitter assigned to said power supply being turned on when said power supply falls below a minimum charge level.

8. The assembly according to claim 4, further comprising an air sensor being coupled to said pipe such that said air sensor is positioned within the distribution duct of the HVAC system wherein said air sensor is configured to be in fluid communication with an interior of the distribution duct, said air sensor being electrically coupled to said control circuit, said control circuit receiving said pump input when said air sensor senses air being moved in the distribution duct.

9. An air freshener assembly being integrated into an air conditioning system of a building for freshening air blown by the air conditioning system, said assembly comprising:

a housing being positionable on a distribution duct of a heating, ventilation and air conditioning (HVAC) system, said housing having a top wall, a bottom wall and an outer wall extending therebetween, said outer wall having a back side and a front side, said front side being open into an interior of said housing, said housing having a divider therein to define a first portion and a second portion of an interior of said housing, said divider being centrally positioned between said top wall and said bottom wall;

a magnet being coupled to said housing, said magnet magnetically engaging the distribution duct for retaining said housing on the distribution duct, said magnet being positioned on said back side of said outer wall of said housing;

a pair of doors, each of said doors being hingedly coupled to said housing for opening and closing said housing, each of said doors having a first surface, a second surface and a first lateral edge, said first lateral edge of each of said doors being hingedly coupled to said front side of said outer wall of said housing, said first surface each of said doors abutting said front side when said doors are closed, said pair of doors including a upper door and a lower door, said upper door having an opening extending therethrough, said upper door being aligned with said first portion of said interior of said housing, said lower door being aligned with said second portion of said interior of said housing;

a pair of handles, each of said handles being coupled to said second surface of a respective one of said doors for opening and closing said doors;

a reservoir being positioned within said housing, said reservoir containing a chemical fragrance, said reservoir being positioned in said second portion of said interior of said housing;

a pump unit being coupled to said housing, said pump unit being in fluid communication with said reservoir wherein said pump unit is configured to pump the chemical fragrance, said pump unit pumping a measured unit of the chemical fragrance each time said pump unit is turned on, said pump unit being in fluid communication with an interior of the distribution duct of the HVAC system wherein said pump unit is configured to release the chemical fragrance into the distribution duct, said pump unit comprising:
- a pipe extending through said back side of said outer wall of said housing and said magnet, said pipe extending into the distribution duct of the HVAC system, said pipe being aligned with said first portion of said interior of said housing;
- a control circuit being positioned in said housing, said control circuit receiving a pump input;
- a pump having an inlet and an outlet, said input being fluidly coupled to said reservoir, said outlet being fluidly coupled to said pipe wherein said pipe is configured to release the chemical fragrance into the distribution duct, said pump being electrically coupled to said control circuit, said pump being turned on when said control circuit receives said pump input, said pump pumping a fixed quantity of the chemical fragrance each time said pump is turned on, said pump being positioned in said first portion of said interior of said housing;
- a power supply being positioned in said housing, said power supply being electrically coupled to said control circuit, said power supply comprising at least one battery, said power supply being positioned in said first portion of said interior of said housing;
- a level sensor being positioned within said reservoir wherein said level sensor is configured to sense the level of chemical fragrance in said reservoir, said level sensor being electrically coupled to said control circuit;
- a pair of light emitters, each of said light emitters being positioned in said housing, each of said light emitters being electrically coupled to said control circuit, each of said light emitters emitting a unique color of light, each of said light emitters being assigned to a respective one of said level sensor and said power supply, said light emitter assigned to said level sensor being turned on when said level sensor senses a minimum level of chemical fragrance in said reservoir, said light emitter assigned to said power supply being turned on when said power supply falls below a minimum charge level, each of said light emitters being aligned with said opening in said door positioned on said first portion of said interior of said housing wherein each of said light emitters is configured to be visible to a user; and
- an air sensor being coupled to said pipe such that said air sensor is positioned within the distribution duct of the HVAC system wherein said air sensor is configured to be in fluid communication with an interior of the distribution duct, said air sensor being electrically coupled to said control circuit, said control circuit receiving said pump input when said air sensor senses air being moved in the distribution duct.

* * * * *